United States Patent [19]

Peterson et al.

[11] Patent Number: 4,769,830
[45] Date of Patent: Sep. 6, 1988

[54] APPARATUS AND METHOD FOR MEASURING BULK DENSITY OF SOLID PARTICLES

[75] Inventors: Richard W. Peterson; Thomas R. Hornack, both of Lower Burrell; Donald C. Morian, Murrysville, all of Pa.

[73] Assignee: Aluminum Company of America, Pittsburgh, Pa.

[21] Appl. No.: 844,569

[22] Filed: Mar. 27, 1986

[51] Int. Cl.$^4$ ............................................. G01N 23/10
[52] U.S. Cl. ........................................ 328/54; 378/57; 378/53
[58] Field of Search ............................ 378/54, 57, 53

[56] References Cited

U.S. PATENT DOCUMENTS

| | | | |
|---|---|---|---|
| 2,843,748 | 7/1958 | Jacobs | 378/54 |
| 3,531,643 | 9/1970 | Bretonniere et al. | 378/54 |
| 4,133,090 | 1/1979 | Peterson | 29/25.18 |
| 4,228,353 | 10/1980 | Johnson | 378/54 |
| 4,283,148 | 8/1981 | Peterson | 366/142 |
| 4,352,288 | 10/1982 | Paap et al. | 378/54 |
| 4,429,410 | 1/1984 | Jury et al. | 378/53 |

FOREIGN PATENT DOCUMENTS 2116587  9/1983  United Kingdom .

OTHER PUBLICATIONS

"Correlation of Raw Material Properties with Binder Content of HS Soderberg Paste", by L. Castonguay and S. K. Nadkarni, *Light Metals*, 1984.

Texas Nuclear catalog entitled "SG Series Density Gauge".

Texas Nuclear catalog entitled "Instruction Manual-SGD & DMD-E-Zcal Density and Mass Flow System".

*Primary Examiner*—Janice A. Howell
*Assistant Examiner*—David P. Porta
*Attorney, Agent, or Firm*—Thomas J. Connelly

[57] ABSTRACT

An apparatus and method for measuring bulk density of solid particles. The apparatus is capable of simultaneously rotating and axially advancing a container containing a sample of solid particles past a source emitting a beam of gamma rays. The gamma rays are absorbed by a detector in proportion to the material density of the solid particles. The absorbed radiation is then compared to a preselected reference value to yield a bulk density for the material. This bulk density can then be used to ascertain the quantity of a binder which needs to be added to a homogeneous mass of coke to form a carbon anode useful in an electrolysis of alumina. The method includes the steps of placing a sample quantity of the solid particles in a container, optionally vibrating the container to settle the particles if desired, and then placing the container on the apparatus so as to be measured. The bulk density measurement is compared to a preselected reference value and this value is then visually displayed.

17 Claims, 5 Drawing Sheets

APPARATUS AND METHOD FOR MEASURING BULK DENSITY OF SOLID PARTICLES

FIELD OF THE INVENTION

This invention relates to an apparatus and method for measuring bulk density of solid particles and more particularly to a method of producing a carbon anode for use in the electrolysis of alumina by measuring the bulk density of the carbon aggregate from which it is formed.

BACKGROUND OF THE INVENTION

The measurement of bulk density of carbon aggregate in the laboratory has been known for many years. This information is used as a guideline for the commercial production of carbon anodes used in the electrolysis of alumina. However, the use of an easy, adaptable method of measuring the bulk density of large commercial quantities of carbon aggregate at a plant site, where the carbon anodes are mass produced, has not existed. Various methods of doing so have been published; two examples are a U.K. patent application, GB No. 2,116,587A, entitled "Production of Carbon Electrodes for Electrolytic Reduction Cells"; and a paper entitled "Correlation of Raw Material Properties With Binder Content of HS Soderburg Paste" by L. Castonguay and S. K. Nadkarni. The paper was published in 1984 from a talk given during an American Institute of Mining, Metallurgical and Petroleum Engineers meeting. It was published by the Metallurgical Society, Warrendale, Pa., in a magazine entitled *Light Metals*. The U.K. patent application teaches a method of producing carbon anodes by establishing a desired green density using a first set formula and adding a binder to fill fractions of the void spaces using a second set formula. The lack of having an onsite measurement apparatus has meant that carbon anodes would vary considerably in desired properties due to the variations of the starting materials, i.e., the coke and the bituminous pitch binder.

From the standpoint of apparatus, several are known but they have been primarily used in the laboratory. U.S. Pat. No. 4,283,148 discloses an apparatus for measuring bulk density of a sample and is assigned to Aluminum Company of America. This apparatus has not been incorporated into the commercial production of carbon anodes since the operation is very labor intensive and requires the test to be run under controlled conditions. A second U.S. Pat. No. 4,133,090, also assigned to Aluminum Company of America, relates to the control of the binder content in carbon anodes. Although this patent relates to the same subject matter, it teaches a method which is different from the present method.

Now an apparatus and method have been invented which provide a quick and accurate way to measure the bulk density of the starting material used in producing carbon anodes.

SUMMARY OF THE INVENTION

Briefly, the present invention relates to an apparatus and method for measuring bulk density of solid particles. The apparatus includes a mechanical mechanism which is capable of simultaneously rotating and axially advancing a container having a sample of carbonaceous coke situated therein. The container is rotated and advanced, at a predetermined rotational and axial speed, past a source emitting a beam of radiation. A detector is oppositely aligned with the source and absorbs the beam of radiation in proportion to the material density of the solid carbonaceous particles. The absorbed radiation is then compared to a preselected reference value to yield a bulk density for the solid particles. The method includes the steps of filling the container with the solid particles, vibrating the container to settle and compact the sample and placing the container on the apparatus to measure the bulk density. The measured bulk density is then visually displayed on a monitor, preferably in digital form.

The general object of this invention is to provide an apparatus and method for measuring bulk density of solid particles. A more specific object of this invention is to provide a method for producing a carbon anode for use in the electrolysis of alumina by measuring the bulk density of the carbon aggregate from which it is formed.

Another object of this invention is to provide an apparatus for measuring bulk density of solid material which can simultaneously rotate and axially advance a sample at a predetermined rotational and axial speed past a density gauge emitting gamma rays.

Still another object of this invention is to provide an inexpensive and simple apparatus for measuring the bulk density of the carbon aggregate for use in producing a uniform and desirable carbon anode.

Still further, an object of this invention is to provide a simple and reliable method for producing uniform carbon anodes at a production facility.

Other objects and advantages of the present invention will become more apparent to those skilled in the art in view of the following description and the accompanying drawings.

DETAILED DESCRIPTION OF THE PREFERRED EMBODIMENT

Figure 1:
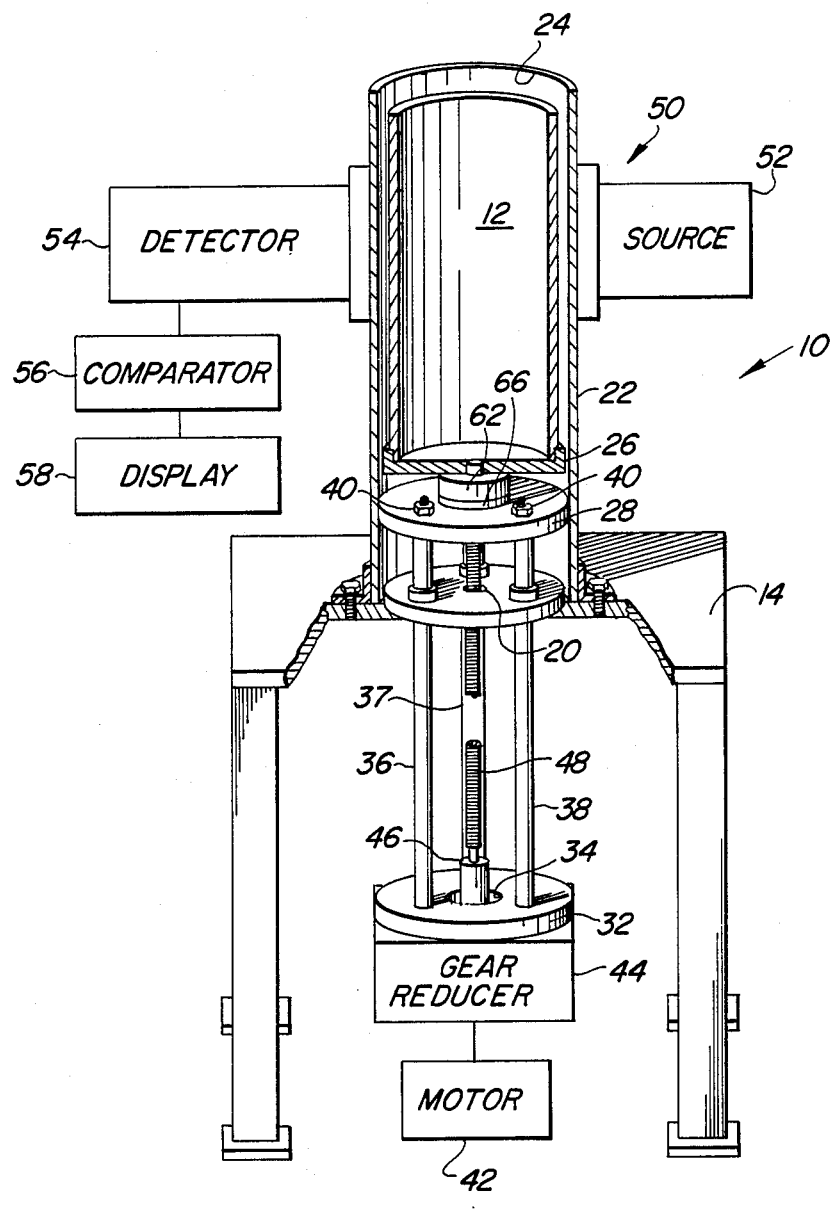
FIG. 1 is a partial sectional view of the apparatus of this invention having the capability of both rotating and axially advancing a receptacle containing a sample quantity of solid particles past a density gauge.
Figure 2:
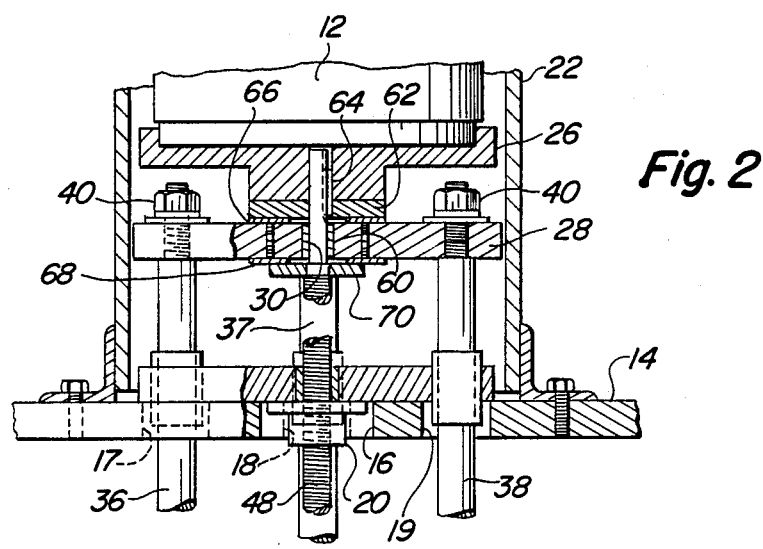
FIG. 2 is an enlarged sectional view of the midsection of the apparatus shown in FIG. 1.

Referring to FIGS. 1 and 2, an apparatus 10 is shown for measuring bulk density of solid particles. The solid particles are placed in a cylindrical receptacle or container 12 and can be vibrated so as to settle and compact the material. With the apparatus 10, the vibration step is optional. The apparatus 10 includes a base member 14 which can be an upstanding stand as shown. The base 14 contains a central bore 16, see FIG. 2, formed therethrough and at least one and preferably three adjacent bores 17, 18 and 19 formed radially outward therefrom. A fixed nut 20 is retained in the central bore 16 so as to be stationary. The nut 20 contains a threaded axial bore formed therethrough, which is not shown. Extending vertically upward from the base member 14 and secured thereto is a cylindrical tube 22. The tube 22 is open at its upper end 24 to permit the container 12 to be inserted therein.

The apparatus 10 also includes a first rotatable plate 26 and a second non-rotatable plate 28, both positioned within the cylindrical tube 22. The first plate 26 is capable of supporting the container 12 while the second plate 28 is positioned below the first plate 26 and has a central bore 30 formed therethrough. A third non-rotatable plate 32 is positioned below the base member 14 and has a central bore 34 formed therethrough. The second and third plates 28 and 32, respectively, are joined together by at least one and preferably three guide rods 36, 37 and 38. The guide rods 36, 37 and 38 pass through the bores 17, 18 and 19 formed in the base member 14 and are permanently fastened to the second and third plates 28 and 32. As is shown in FIGS. 1 and 2, the attachment is via a threaded engagement secured by hex nuts 40. However, other types of fasteners can be used, as are well known to those skilled in the art.

The apparatus 10 further includes a drive motor 42 which is preferably a variable speed and reversible direct current (D.C.) motor. The drive motor 42 is connected via a gear reducer 44 which in turn is attached by a coupling 46 to an elongated screw 48. The motor 42 can be permanently or temporarily secured to the lower portion of the third plate 32. The elongated screw 48 is secured at its upper end to the first plate 26. The elongated screw 48 also passes through the central bore 30 formed in the second plate 28 and is axially movable through the fixed nut 20. The screw 48 is designed to have a given pitch, such as 0.20 inches per revolution, so that as the screw 48 is rotated by the motor 42 it advances through the fixed nut 20. Such action will rotate and axially advance the first plate 26 upward within the tube 22. By coupling the gear reducer 44 between the motor 42 and the screw 48 and by changing the lead of the screw 48, one can adjust the rotational and axial speeds of the first plate 26. For example, if one started with a motor operating at 1750 revolutions per minute and a gear reducer of approximately 20:1, one could obtain an axial speed of approximately 17.5 inches per minute with a screw pitch of 0.20 inches per revolution. Experimentation has shown that a more preferred measurement of a sample can be obtained by slowing down the rpm to approximately 22.5 revolutions per minute while using an axial speed of approximately 4.5 inches per minute. However, the rotational and axial speeds can vary depending upon the type of sample being measured and the capabilities of the density gauge. For most measurements, a rotational speed of between 20 and 100 rpm and an axial speed of between 4 and 20 inches per minute will suffice.

A density gauge 50 is perpendicularly aligned with and mounted on the outside circumference of the cylindrical tube 22 to measure the density of the solid particles within the container 12. The density gauge 50 includes a source 52 which is capable of emitting radiation, particularly gamma rays, through the solid particles contained in the container 12 and a detector 54 for receiving the emitted radiation. The density gauge 50 is commercially available from Texas Nuclear, a subsidiary of Ramsey Engineering, P.0. Box 9267, Austin, Tex. 78766. The SG Series density gauge is suitable for this application. Since density is a non-linear function of signal level, the gauge can operate in two different modes. In one mode, called the normal mode, the system averages the detector signal and then computes a density. In the other mode, called the scan mode, the system continually converts the signal to density and then averages the density. The scan mode is useful where the density varies greatly during the averaging period while the normal mode usually produces the best result where the density of the material is essentially constant during the measurement.

Once the detector 54 has absorbed the gamma rays emitted by the source 52, the detected gamma rays are compared to a preselected reference value to yield a bulk density for the solid particles. The reference value for a given type of particle would be measured in a laboratory using known techniques. The density of a sample is equal to its weight over its volume. In the process of preparing carbon anodes for use in an electrolytic cell, it is very easy to calculate the density of a carbonaceous aggregate and also the density of a bituminous pitch coming from a particular supply source. Once this information is known, it can be used as the reference value for comparison by a comparator 56.

Having compared the measured bulk density to a reference value, it is beneficial to visually display it on a digital or graphical display device 58. In a commercial environment where a range of tolerances can be tolerated, an operator can visually inspect the measured bulk density and if it lies within a predetermined operational range, the operator can continue to perform his other duties. Should the bulk density of the measured quantity fall outside of the range, the operator can take appropriate steps to adjust the input to bring the bulk density back within the desired range.

Referring again to FIG. 2, the apparatus 10 is designed such that the second plate 28 is secured by a bushing 60 to the elongated screw 48 in order to reduce friction therebetween. As shown, a steel plate 62 is attached to a lower surface of the first plate 26 by a key 64 so as to rotate therewith. Positioned between the steel plate 62 and the second plate 28 is a wear plate 66, constructed out of a soft material such as bronze, which is screwed into the second plate 28. The wear plate 66 is designed to wear down as friction occurs between the rotating first plate 26 and the non-rotating second plate 28. Once the wear plate 66 has been reduced in thickness to a predetermined height, it can simply be replaced with another plate. For purposes of support, a second wear plate 68 is attached to the opposite surface of the second plate 28 and is held in place by a support plate 70.

Figure 3:
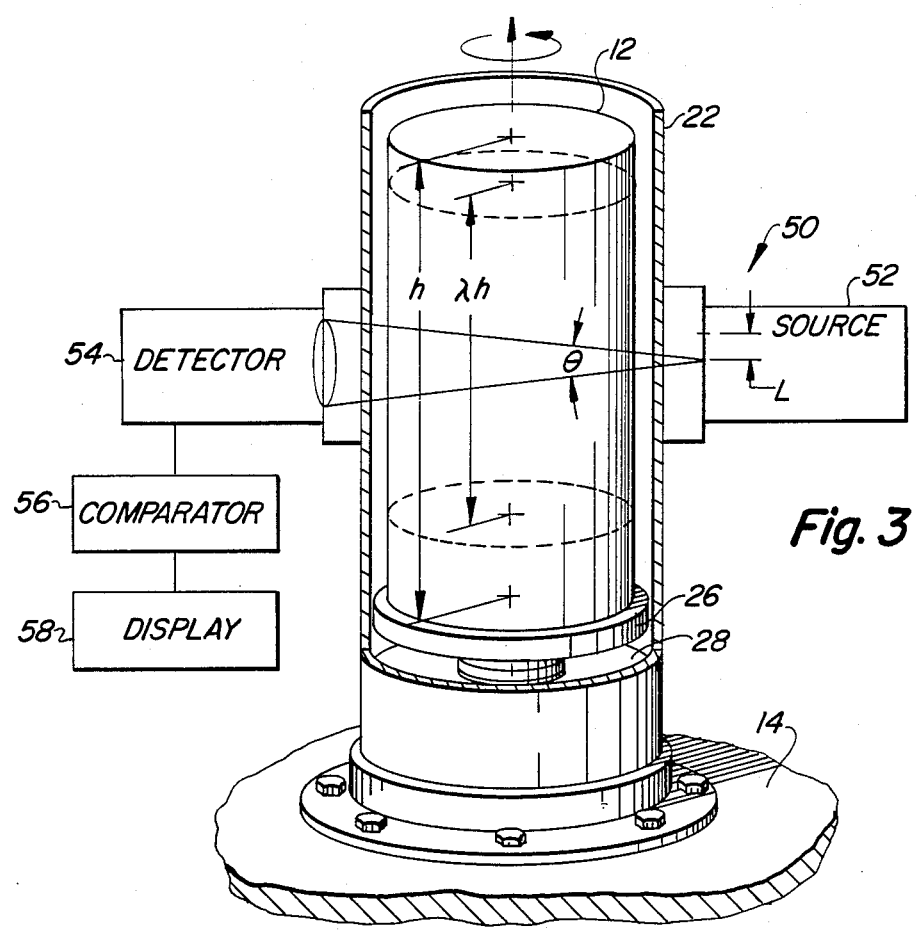
FIG. 3 is a sectional view of the receptacle relative to a beam of gamma rays emitted by the density gauge.

Referring to FIG. 3, the density gauge 50 is shown emitting a conical beam of gamma rays from the source 52 which passes through the cylindrical tube 22, the container 12 and the sample of solid particles contained therein. The gamma rays will be absorbed by the detector 54 in proportion to material density of the solid particles. Since the sample is being rotated and advanced vertically upward through the conical beam from the source 52, various particles will be subjected to the gamma rays over a period of time. In order to obtain a more accurate measurement, it has been established that the cone angle $\theta$ for the emitted beam be approximately 6° and that the central two-thirds or three-fourths of the height (lambda h) of the container 12 be measured. For example, if the height (h) of the container 12 was 18 inches, only the central or middle 12 to 15 inches would be subjected to the gamma rays.

This will eliminate the possibility of emitting the gamma rays through a void space such as would occur when the top surface of the sample became aligned with the central axis of the conical beam. For purposes of time and efficiency, it has been found that by advancing the sample upwardly through the conical beam of gamma rays that an accurate measurement can be obtained. Alternatively, the sample can be measured in the downward direction or during both the upward and downward travel past the conical beam.

The method of measuring bulk density of solid particles, particularly particles of different size, will now be explained. Although a calcined coke bulk density test is simple, basic understanding of the principles involved is essential to the development of a useful test. It must be understood that the test results are influenced by particle size and shape as well as by porosity and inherent density (real density) of the material being tested. If the particle size is not closely controlled, ill-defined values will be obtained. For example, fine particles contained in interstices among coarse particles will add weight without increasing value. Hence, a bulk density value for a given coke can be increased greatly by changing from a closely sized coarse particle network to a broad particle size distribution. Moreover, with closely sized fractions of calcined petroleum coke, bulk density tends to increase with decreasing particle size. This occurs because such cokes usually contain pores and fissures of a variety of sizes. As large pores are annihilated on reduction to smaller particle sizes, density increases. Another factor influencing bulk density is particle shape. Spherical particles will pack tighter than plate-like or needle-like particles.

The differences caused by the size and shape of the particles can be minimized by crushing the particles to a predetermined size before they are placed in the container 12. This does not mean that all of the particles have to be of the same size, but that the particles will be no larger than some given mesh size. In the production of carbon anodes, the Tyler mesh is a standard used by the industry. Vibration of the particles within the container 12 will also help to compact and compress the sample so as to yield a more meaningful bulk density measurement. As stated earlier, the vibration step is optional, and when the sample is not vibrated the measurement is referred to as "loose bulk density". After being vibrated, the container 12 is placed on the apparatus 10 and is adjusted such that the source of radiation will pass through the sample approximately 1/6 of the way down from its upper surface. The container 12 is then rotated by activation of the motor 42 while the conical beam of radiation passes through the sample. It should be noted that for best results the source 52 and the detector 54 should be perpendicularly aligned to the sample contained in the container 12 and be oppositely aligned to one another. It is also a matter of choice whether the density gauge 50 first averages the detected radiation signal and then computes the density or continually converts the detected radiation signal to a density value before averaging.

Figure 4:
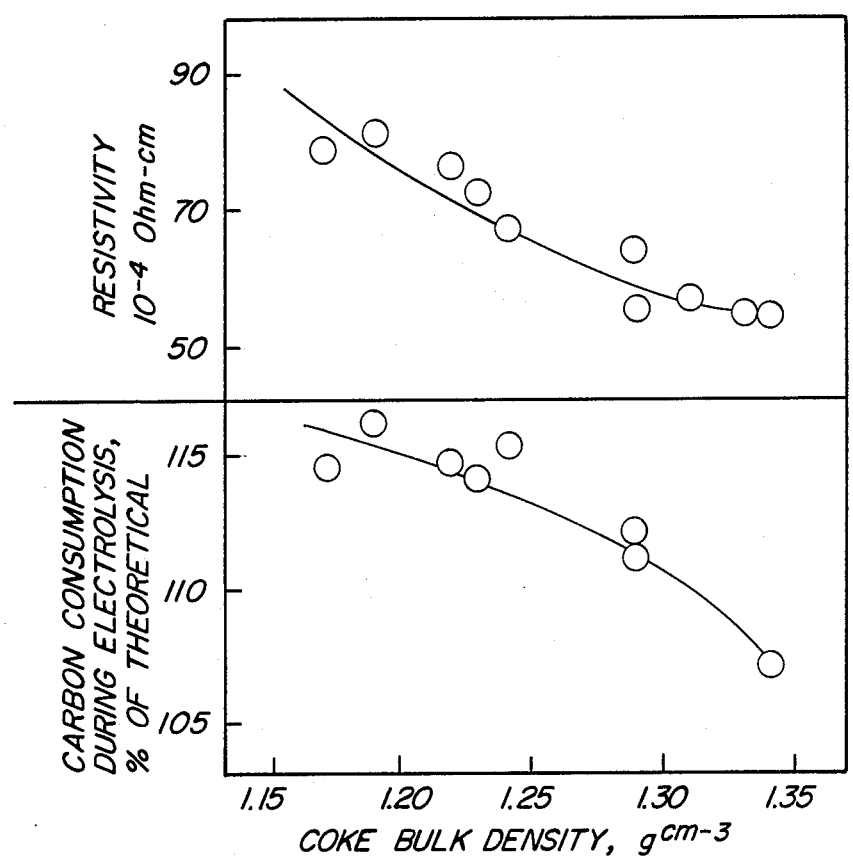
FIG. 4 is a graph of the resistivity and carbon consumption during electrolysis of an anode for electrolytic production of aluminum as a function of the bulk density of coke particles used in manufacturing the anode.

In the aluminum industry, the quality of carbon anodes can be optimized by producing them from a mixture of coke particles having a particular bulk density. The graphs in FIG. 4 show that both resistivity and carbon consumption during electrolysis decreases as a function of the bulk density of the coke particles used as the raw material for the anodes. In order to enhance the properties of the anodes and to insure their longevity, it is desirable to have available a method and apparatus for quickly and easily measuring the bulk density of the carbonaceous material so that adequate control is maintained over the finished product. By inserting the bulk density measurement into the method of producing carbon articles and by adding a specific amount of a binder to the carbonaceous aggregate in relation to the bulk density of the carbonaceous aggregate, essentially identical carbon articles having preselected desired properties can be produced.

Figure 5:
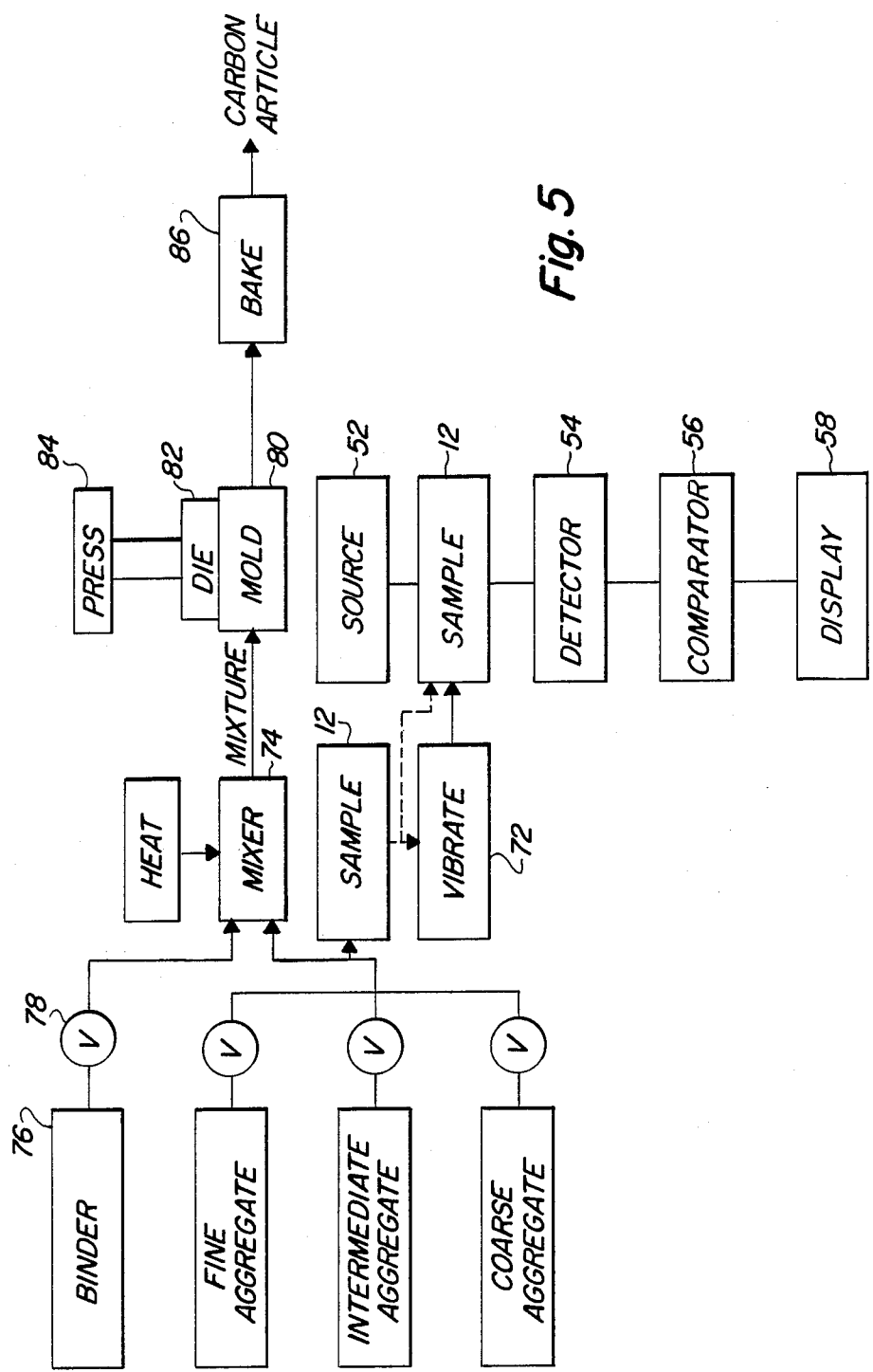
FIG. 5 is a schematic diagram illustrating a method for producing a carbon anode for use in the electrolysis of alumina.

Referring to FIG. 5, a method of producing a carbon article is schematically represented. The method starts with the combination of fine, intermediate and coarse size carbon aggregates in a ratio of about 35–45 weight percent fine, about 15–25 weight percent intermediate and about 35–45 weight percent coarse to form a homogeneous mass. As used herein, a coarse aggregate particle would not pass through a screen having a Tyler mesh of 28, an intermediate aggregate particle would pass through a screen having a Tyler mesh of 28 but not 100 mesh, and a fine aggregate particle would pass through a screen having a Tyler mesh of 100 or more. A small sample of the homogeneous mass is then placed in the container 12 and is vibrated by a vibrator 72 to settle and compact the solid particles. The container 12 is then placed on the bulk density measurement apparatus 10 and the bulk density is measured. This measured value is then compared by the comparator 56 to a predetermined reference value to yield a bulk density for the sample and this value is displayed on display unit 58. Knowing the bulk density of the sample, the operator can now add a specific amount of a binder 76 to the homogeneous mass by opening a valve 78. A typical binder for the production of carbon anodes is a bituminous pitch such as coal tar pitch. The coal tar pitch is an organic pitch very high in carbon content having a softening point of approximately 110° C. and having a low viscosity between 145° and 170° C. Petroleum pitch can also be used as the binder. Knowing the composition of the binder and its physical constants, the operator will add a set amount depending upon the final properties he desires in the final carbon article. For carbon anodes, 16 weight percent pitch to coke will produce an acceptable anode. The homogeneous mass and binder 76 are then mixed in a mixer 74 in the presence of heat, preferably a temperature of about 100° to 170° C., and more preferably a temperature of about 120° to 150° C., for a short period of time. The resultant mixture is a highly viscous material that is routed to a mold 80. A die 82 is then pressed by a press 84 to form the material into a desired configuration. From here, the formed material is routed to an oven or furnace 86, such as a ring furnace, where it is baked for a period of time at a temperature of between 1000° and 1150° C. Upon removal, a carbon anode is produced which is ready for use in an electrolytic reduction cell.

Figure 6:
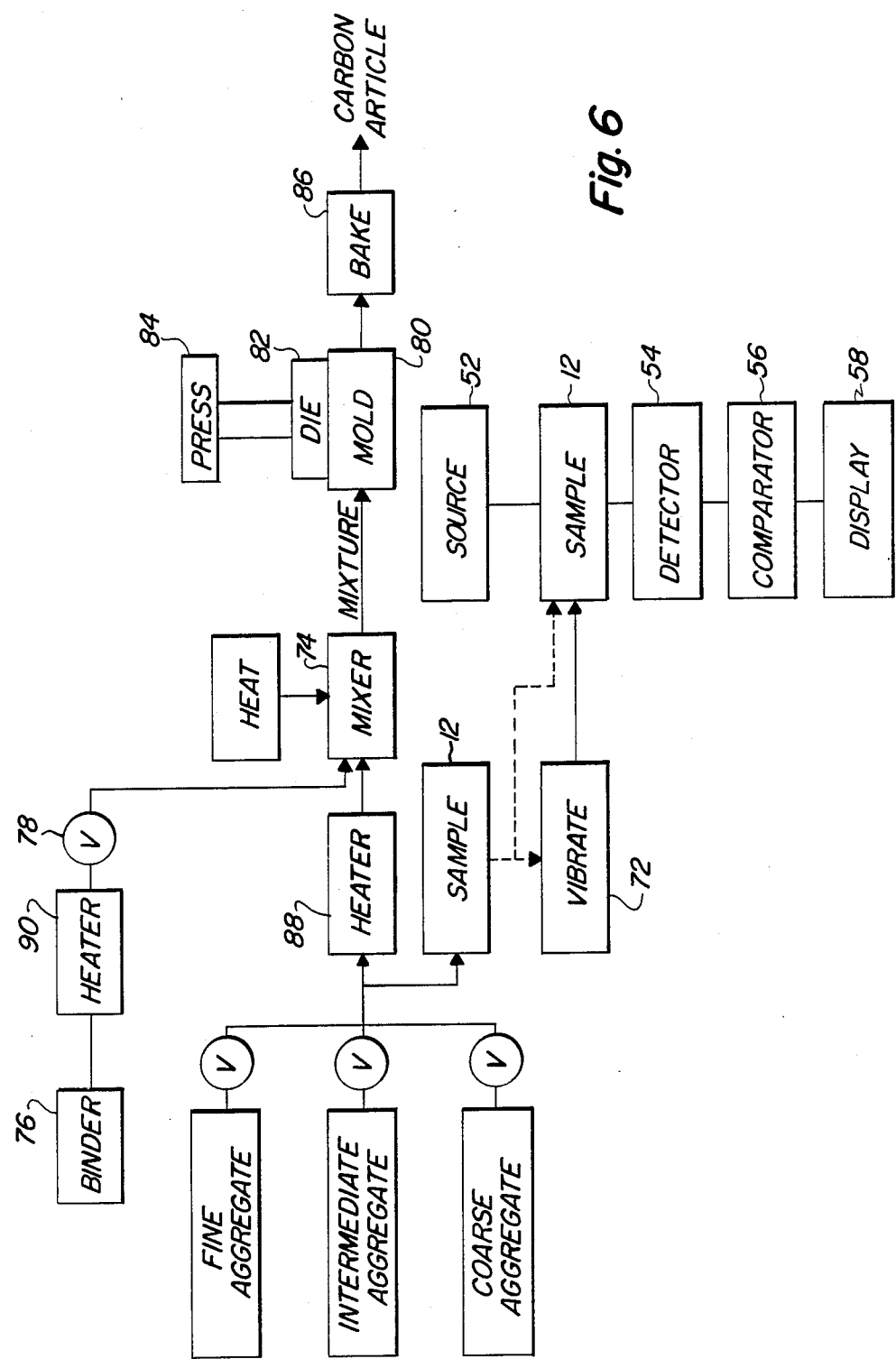
FIG. 6 is a schematic diagram illustrating an alternative method for producing a carbon anode.

Referring to FIG. 6, an alternative method for producing a carbon anode is depicted. In this schematic, the equipment is designated by the same numerals as used in FIG. 5. The method differs from the previously described method in that the homogeneous mass of coke is heated by a heater 88 to a temperature between 100° and 130° C. before it enters the mixer 74. Also, the binder 76 is heated by a heater 90 to a temperature above 110° C., and preferably to a temperature between 160° and 180° C., before it is added to the mixer 74. This preheating of both the coke and the binder 76 facilitates the mixing process and shortens the time needed before the resultant mixture can be sent to the mold 80.

While the invention as been described in conjunction with a specific embodiment, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. An apparatus for measuring bulk density of solid granular particles, comprising:
   (a) a base member having a central bore and at least one other bore formed therethrough, said central bore having a fixed nut retained therein, and a stationary cylindrical tube extending vertically upward from said base member, said tube being open at an upper end to receive a container holding a quantity of said solid granular particles;
   (b) a rotatable first plate for supporting said container and a non-rotatable second plate both positioned within said cylindrical tube, said second plate positioned below said first plate and having a central bore formed therethrough, a non-rotatable third plate positioned below said base member and having a central bore formed therethrough, said second and third plates joined together by at least one guide rod which passes through said other bore formed in said base member and an elongated screw connecting said first plate to a drive motor and being axially movable through said fixed nut, rotation of said screw by said drive motor causing simultaneous rotation and axial displacement of said container past a source emitting a conical beam of radiation;
   (c) a detector axially aligned with said source of radiation and positioned on an opposite side of said cylindrical tube, said detector being capable of absorbing gamma ray signals in proportion to the material density of said solid particles; and
   (d) means for comparing said detected gamma ray signals to a preselected reference value to yield a bulk density for said solid granular particles.

2. The apparatus of claim 1 wherein said source is perpendicularly aligned to said container and emits a conical beam of gamma rays through said solid granular particles contained in said container.

3. The apparatus of claim 1 wherein said means for comparing said detected radiation to a preselected reference value includes a computational device which averages said detected gamma ray signals to arrive at a specific density.

4. The appratus of claim 1 wherein said rotational speed of said container is between 20 and 100 rpm and said axial speed is between 4 and 20 inches per minute.

5. The apparatus of claim 1 wherein said conical beam of radiation emitted from said source has a cone angle of approximately 6 degrees.

6. The apparatus of claim 1 wherein said means for comparing said detected radiation to a preselected reference value includes a computational device which continually converts said detected gamma ray signals to density and then averages said density.

7. The apparatus of claim 1 wherein said source of radiation is mounted on said cylindrical tube.

8. The apparatus of claim 1 wherein said detector is mounted on said cylindrical tube.

9. A method of measuring bulk density of solid granular particles comprising the steps of:
   (a) providing an apparatus having a base member with a central bore and at least one other bore formed therethrough, said central bore having a fixed nut retained therein and a stationary cylindrical tube extending vertically upward from said base member, said tube being open at an upper end to receive a container capable of holding a quantity of said particles, a rotatable first plate for supporting said container and a non-rotatable second plate both positioned within said cylindrical tube, said second plate positioned below said first plate and having a central bore formed therethrough, a non-rotatable third plate positioned below said base member and having a central bore formed therethrough, said second and third plates joined together by at least one guide rod which passes through said other bore formed in said base member, and an elongated screw connecting said first plate to a drive motor and being axially movable through said fixed nut, rotation of said screw by said drive motor causing simultaneous rotation and axial displacement of said container past a density gauge having a source emitting a conical beam of radiation and a detector capable of absorbing said emitted radiation;
   (b) filling said container with a quantity of particles;
   (c) placing said container in said cylindrical tube and simultaneously rotating and axially advancing said particles past said density gauge at a preselected speed;
   (d) emitting a conical beam of gamma rays from said source through said particles and absorbing said emitted rays in proportion to the material density of said particles;
   (e) comparing said detected gamma rays to a preselected reference value to yield a bulk density for said particles; and
   (f) visually displaying said measured bulk density.

10. The method of claim 9 wherein said density gauge is perpendicularly aligned with said container and emits a continuous conical beam of gamma rays at a cone angle of approximately 6 degrees through said solid particles.

11. The method of claim 9 wherein said solid particles are first crushed to a predetermined size before being placed in said container and are then vibrated to settle and compact said particles.

12. The method of claim 9 wherein said density gauge averages said detected gamma rays and then computes a density.

13. The method of claim 9 wherein said density gauge continually converts said detected gamma ray signals to density and then averages said density.

14. An apparatus for measuring bulk density of a plurality of different size solid particles, said apparatus comprising:
   (a) a base member having a central bore and at least one adjacent bore formed therethrough,
   (b) a fixed nut retained in said central bore of said base member,
   (c) a cylindrical tube secured to a top surface of said base member and extending vertically upward therefrom, said tube being open at an upper end to receive a container at least partially filled with said solid particles, (d) a first rotatable plate positioned within said tube which is capable of supporting said container and a second non-rotatable plate positioned within said cylindrical tube below said first plate, said second plate having a central bore formed therethrough, (e) a non-rotatable third plate positioned below said base member and having a central bore formed therethrough, said second and third plates joined together by at least one guide rod, said guide rod passing through said other bore formed in said base member, (f) a drive motor, (g) an elongated screw coupled at one end to said drive motor and secured at an opposite end to said first plate, said screw passing through said central bore of said second plate and being axially movable through said fixed nut, rotation of said screw by said drive motor causing both rotational and axial displacement of said container supported on said first plate, (h) a density gauge perpendicularly aligned with and mounted on said cylindrical tube, said density gauge having a source capable of emitting a beam of gamma rays through said solid particles contained in said container and a detector capable of absorbing said emitted gamma rays in proportion to the material density of said solid particles, (i) means for comparing said detected gamma rays to a preselected reference value to yield a bulk density for said solid particles, and (j) display means for providing a visual indication of said measured bulk density.

15. The apparatus of claim 14 wherein said drive motor is a variable speed, D.C. motor.

16. The apparatus of claim 15 wherein a gear reducer is connected between said drive motor and said elongated screw.

17. The apparatus of claim 14 wherein said first and second plates are axially secured to said elongated screw so as to move in unison and a metal wear plate having a central bore formed therethrough is mounted therebetween to reduce wear between said rotatable first plate and said non-rotatable second plate.

* * * * *